United States Patent [19]

Oliver Ruiz et al.

[11] Patent Number: 6,110,699
[45] Date of Patent: Aug. 29, 2000

[54] PROCESS FOR PRODUCING 6-AMINO-PENICILLANIC ACID AND PHENYLACETIC ACID

[75] Inventors: Manuel Oliver Ruiz; Nieves Fraile Yecora; Emiliano Gonzalez De Prado; Alejandro Vitaller Alba, all of León; Francisco Salto Maldonado, Madrid, all of Spain

[73] Assignee: Antibioticos, S.A., Madrid, Spain

[21] Appl. No.: 08/952,311

[22] PCT Filed: Mar. 14, 1997

[86] PCT No.: PCT/ES97/00066

§ 371 Date: Feb. 25, 1998

§ 102(e) Date: Feb. 25, 1998

[87] PCT Pub. No.: WO97/35029

PCT Pub. Date: Sep. 25, 1997

[30] Foreign Application Priority Data

Mar. 15, 1996 [ES] Spain ................................. 9600637

[51] Int. Cl.[7] .................................................. C12P 37/00
[52] U.S. Cl. .................. 435/43; 435/44; 435/46
[58] Field of Search .................. 435/47, 46, 43, 435/44

[56] References Cited

U.S. PATENT DOCUMENTS

| | | | |
|---|---|---|---|
| 3,787,288 | 1/1974 | Miyamura | 435/47 |
| 3,887,432 | 6/1975 | Cawthorne . | |
| 5,500,352 | 3/1996 | Lopez | 435/44 |

FOREIGN PATENT DOCUMENTS

| | | |
|---|---|---|
| 1110686 | 10/1995 | China . |
| 268591 | 7/1990 | Czechoslovakia . |
| 0069869 | 1/1983 | European Pat. Off. . |
| 1589113 | 4/1970 | France . |
| 277088 | 3/1990 | German Dem. Rep. . |
| 59-082097 | 5/1984 | Japan . |
| 1212551 | 11/1970 | United Kingdom . |

OTHER PUBLICATIONS

Batchelor et al., Proc. Roy. Soc. (London) B154, 1961, pp. 498–508.

Chemical Abstracts, vol. 101, No. 15 (1984) Columbus, Ohio Abstract No. 128857 "6 Aminopenicillanic Acid" Abstract & JP 59082097 A (Toyo Jozo Co., Ltd.) May 11, 1984.

Chemical Abstracts, vol. 116, No. 17 (1992) Columbus, Ohio Abstract No. 168965 , "Separation of Enzymes from Fermentation Medium from Penicillin Productikon by Ultrafiltration" Abstract & CS 268591 A (P. Brokes et al.) Jul. 31, 1990.

Database WPI Section Ch, Week 9043 Derwent Publications Ltd. London, GB, Class B02, AN 90–321113 & DD 277088 A (VEB JENAPHARM) Mar. 21, 1990.

Chemical Abstracts No. 258679 of CN 11106861 Dated Nov. 19, 1996.

*Primary Examiner*—Irene Marx
*Attorney, Agent, or Firm*—Ladas & Parry

[57] ABSTRACT

Alternative process for obtaining 6-aminopenicillanic acid. The process comprises replacing the stages of extraction with organic solvents and isolation and separation of the intermediate penicillin salt as a solid by a process of ultrafiltration of the culture broth in at least 2 successive stages. The first stage has a cut-off for molecular weights of 20,000 Dalton and the second, 2000 Dalton. Subsequent to the enzyme conversion stage the products from that stage are subjected to a series of anionic exchange chromatography steps.

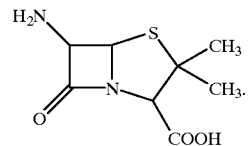

12 Claims, No Drawings

PROCESS FOR PRODUCING 6-AMINO-PENICILLANIC ACID AND PHENYLACETIC ACID

This application was filed under 35 USC 371 as the national phase of PCT/ES97/00066 filed Mar. 14, 1997.

The invention comprises a new alternative process for obtaining and fundamentally recovering 6-aminopenicillanic acid (6-APA) by ultrafiltration of the culture broth and fractionated recovery of the enzyme hydrolysis products using ion exchange resins.

STATE OF THE ART

One of 6-APA is an integral b-lactam compound of the various penicillins. Penicillins consist of the heterocyclic group consisting of a thiazolidine ring (with 5 members including one sulphur atom) fused with a beta-lactam ring (with 4 members), which are distinguished from each other by the nature of the side chain attached to the amine group in position 6 through a peptide link. The formula of 6-APA is:

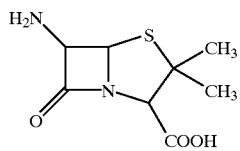

Even when the formation and presence of 6-APA has been detected in the course of the fermentation of penicillins, and consequently in the broth, and given that the quantities are merely traces, the processes in use are based on the concept that the manner of obtaining this product should proceed by other routes and usually follow the following sequence.

The fermentation of microorganisms of the *Penicillium chrysogenum* type under optimum conditions for use of nutrients and energy makes it possible to obtain the greatest output of the corresponding penicillin, depending on the precursor used, which is normally PenG or PenV. Other reactions forming other metabolites, as well as the difficult-to-avoid degradation reactions of penicillin to penicillanic acid, oxidation of the phenylacetic acid precursor to oxidized derivatives such as o-hydroxyphenyl acetic acid, which must be controlled, take place during this type of fermentation and alongside the penicillin biosynthesis reactions.

Once fermentation is complete, the culture broth contains the compounds mentioned plus the biomass of the microorganism and the normal process basically consists of removing this biomass by known physical procedures: filtration, centrifuging, etc., to yield a filtered broth which has been clarified to a greater or lesser extent and contains no biomass.

Starting from this solution the most widely-used process comprises performing a liquid-liquid extraction at acid pH using appropriate equipment capable of dealing with the emulsions which form between the broth and the organic solvent, which in most cases require the use of surfactants. The solvents normally used, which have to be immiscible with the broth, include: esters, of the ethyl acetate, n-butyl acetate, etc., type; ketones, of the methyl isobutyl ketone type; alcohols of the n-butanol, etc., type. The efficiency of this stage is affected by temperature control, loss of activity in the broth, which is exhausted both through deactivation at acid pH and the physical loss connected with inadequate separation of the organic phase, which may remain included, and which in any case requires costly equipment, the use of surfactants, with consequences on costs and environmental problems, and the use of solvents.

The organic-rich phase obtained in this way normally requires purification stages: centrifuging, washing, treatment with active carbon, etc., to remove impurities. Penicillin is crystallized out from this organic phase by introducing the corresponding cation, normally $K_+$, in an appropriate form to render it insoluble and to allow it to be subsequently separated by filtration, ending with drying, packaging and inspection.

The resulting penicillin, which normally has a high degree of purity, even though it is not free from some impurities which can give rise to problems on some occasions, is converted into 6-APA by the reaction of removing the side chain linked to the amino group in position 6. This reaction was initially performed by chemical processes, but now it is frequently being carried out through enzyme processes using enzymes of the penicillin acylase or amidase (3.5.1.11) type immobilized by different procedures, and which in brief can be grouped together as trapping, ionic or covalent bonding to a support, as described for example in Spanish patent No. 369,125. The source of the enzyme is variable, and of the various microorganisms of the bacterial type it is accepted that the acylase from *Escherichia coli*, from strains of this species which have been industrially improved, is the most frequently used. The function of this enzyme is to recognize the side chain and break the peptide link joining it to the 6-APA nucleus in a reaction which normally takes place in aqueous phase with control of the pH at slightly alkaline values. Subsequently the 6-APA is isolated by adjusting the pH to that which corresponds to the isoelectric point, while the side chain component is first solvent-extracted, followed by a further aqueous-phase extraction for reuse as a precursor in the fermentation itself, following appropriate tests.

Subsequently a stage of recovery of the 6-APA product present in the crystallization mother liquors may be required, through concentration by reverse osmosis to concentrations which make crystallization easier.

The problems inherent in the state of the art, which this invention overcomes, are of various kinds. On the one hand the use of solvents and de-emulsifiers (fundamentally quaternary ammonium salts) gives rise to major environmental problems with wastes, the treatment of which affects costs, the complexity of the process and equipment and installations involved in it.

Likewise the fractionated preparation of powder solids presents a high risk of contamination in the final product.

This invention is designed to overcome some of the problems which now exist in the production of 6-aminopenicillanic acid. Specifically this invention simplifies the process of production by eliminating stages. Starting from the filtered penicillin broth, even though the possibility of direct use of the fermentation broth itself cannot be ruled out, it is felt that the stages of:

extraction with organic solvent isolation and separation of the intermediate penicillin salt as a solid whose purpose, in the final analysis, is to prepare an intermediate product having a suitable level of purity to permit subsequent enzyme hydrolysis under conditions of speed and economy which justify this stage, are not essential as such, and give rise to the problems mentioned above in respect of equipment, costs and environmental requirements.

The alternative achieved by this objective of purifying the penicillin in solution, which can be used for enzyme conversion to 6-APA, is the subject-matter of this invention. The removal of impurities, which is achieved by extraction with an organic solvent and the additional purification resulting from crystallization, is replaced by an ultrafiltration (UF) stage.

Based on the fact that UF is a technique for the separation of dissolved molecules according to their size fundamentally through the step of corresponding dissolution through a membrane which acts as a filter barrier, with openings of a sufficiently small size to retain all or most large molecules or molecules larger than the openings in the membrane and permitting passage of the solvent and molecules of small size or of a size smaller than the molecular cut-off, a fraction which is enriched with large molecules—the retained fraction—and a solution or permeate which is enriched in small molecules and which contains no large molecules, is obtained in this way. A determining factor in achieving this separation, jointly with the effects of pressure, temperature and pH of the solution, is the chemical nature of the membrane, and the actual size of the openings, which is reflected in the cut-off value for molecular size.

Although the application of UF in the scope of biotechnology is known, e.g. ZA 8003750, JP 56148683, JP 61070999, WO 8707525, WO 8704169, it is felt that performing the operation while fulfilling the requirement of achieving maximum purification under continuous process conditions, in such a way that the distance travelled between entry of the broth and output of the permeate/diafiltrate is a minimum, with the result that with adequate control of the temperature below 20° C. the effects of possible microbial contamination are reduced and the stability of the dissolved product is increased, is worthy of emphasis.

On the basis of this end of conversion, in which the known alternatives bring about the separation of 6-APA through crystallization, leaving a solution of AFA from which it can be recovered by liquid-liquid extraction, it is felt that combining in sequence the end of conversion with a stage of purification using resins achieves not only isolation of the 6-APA and AFA, but also their simultaneous separation in one operation, even though sequential, through control of elution. At this point it must be pointed out that the references relating to the use of resins described in the literature, which use strongly basic resins (F. R. Batchelor et al., Proc. Roy. Soc. Biochemistry—1961—vol. 154, 498), are restricted to the isolation and purification of 6-APA alone, independently of the other accompanying compounds.

The 6-APA eluate makes it possible to achieve a majority separation of this product by crystallization, and the recovery of another additional quantity of 6-APA from the mother liquors by increasing the concentration by reducing the volume.

DESCRIPTION OF THE INVENTION

The invention constitutes an alternative to known processes for obtaining 6-APA, improving its costs, its yields, simplifying the equipment used and increasing its environmental requirements through the following improvements:

Conditioning the filtered or centrifuged broth through stages of treatment with ultrafiltration membranes in two stages:
Stage 1 with a nominal cut-off of the order of 20,000 Dalton
Stage 2 with a nominal cut-off of the order of 2000 Dalton
In the case of penicillin broths the best purification effect using this principle of UF is achieved using polysulphone or polyether sulphone membranes with a cut-off of the order of 20,000 Dalton, combined with the effect of nanofiltration using membranes with a molecular cut-off of the order of 2000 Dalton. Nanofiltration is characterized specifically by the rejection of divalent $Ca^{2+}$ and $Mg^{2+}$ salts in the form of chlorides and sulphates and solution contaminants. In this way the broth can be purified by removing protein and metabolite components of high molecular weight, together with the remains of the biomass and insoluble compounds. The filter cake obtained, which is rich in metabolites and enzymes, can further be used as an animal feedstuff.

Eliminating the stage of purification by extraction with an organic solvent, together with that of isolation and separation of the intermediate penicillin salt as a solid.

Performing enzyme conversion under conditions of rapid conversion on the penicillin solution purified by UF, using a fixed enzyme. The permeate resulting from the ultrafiltration stage comprises a solution of penicillin G together with other soluble compounds. Through a storage vessel the metering of enzyme/substrate can be coordinated in such a way that the hydrolysis time can be considerably reduced and operation is quasi-continuous. As a result of the action of the enzyme a solution of 6-APA, AFA and other compounds, fundamentally inorganic salts which do not substantially affect the behaviour of the enzyme, is obtained.

Simultaneous recovery and successive separation of the products of enzyme hydrolysis using exchange resins in a way which makes it possible to repeat the process and reuse the side chain in the fermentation, as well as bring about the independent crystallization of 6-APA or the acquisition of a solution of this compound under conditions in which conversion into corresponding derivatives of the ampicillin, amoxycillin type can be continued by enzyme reaction with the corresponding side chain activated in the appropriate form and with the relevant enzyme.

The following examples of its implementation are provided by way of a practical embodiment of the invention without being in any way restrictive:

EXAMPLE 1

The biomass was separated out from a fermentation broth by filtration and the filtered broth was subjected to ultrafiltration in such a way that it was concentrated of the order of 30-fold, continuously, using a 20,000 Dalton membrane. The retained fraction was diafiltered to reduce the loss of penicillin activity. A second UF pass using a 2000 Dalton membrane was performed on the permeate plus diafiltrate, likewise as a continuous process.

This yielded a permeate with approximately 20 g/l of penicillin which had been sufficiently purified to allow enzyme conversion to be carried out in a recycling circuit in such a way that the penicillin was converted into 6-APA and phenylacetic acid with control of the reaction by keeping the pH constant in operations which required some 60–90 minutes.

The corresponding solution at the end of the enzyme conversion, consisting of a mixture in the aqueous phase of phenylacetic acid (AFA) in a concentration of the order of 7 g/l plus the 6-APA in a concentration of the order of 10 g/l, together with the other accompanying products resulting from fermentation, was passed through a suite of resins comprising a first column containing a resin of the non-ionic type, for example XAD 16, plus a further four columns packed with strong anionic resin of the SA 11A type in the form of acetate.

The feed to column XAD 16 was such that a total of approximately 13 v/v of the final conversion solution was passed through in a descending flow at a rate of the order of 2 v/v.h and in such a way that the output from this resin provided the feed to the top of the first anionic resin column. Similarly the output from the bottom of this first anionic column provided the feed to the top of the second anionic resin column and so on until it had passed through the set of all four columns. When delivery to the non-ionic column was complete, it was flushed with 1 v/v of water, which was added to the volume fed to the first anionic resin column.

At this point it could be considered that the XAD 16 resin had performed its task by checking that it did not absorb AFA or 6-APA, and could be regenerated, even though the corresponding wastes produced were of no use. It was found that a residue containing of the order of 4–10 g/l of solids requiring disposal was eluted.

6 v/v of 0.05N NaCl solution was passed through the first anionic column in such a way that the quantity of 6-APA retained was displaced and fed to the second column. This in turn was flushed with 2.5 v/v of the same solution using a similar procedure. In this way the first and second columns became selectively charged with AFA while the third and fourth columns were charged with 6-APA. Each column was then eluted separately, using a solution of NaOH for the first and second columns, which makes it possible to prepare a solution of AFA which can be reused for fermentation, and using 1M NaCl for the third and fourth columns in the proportion 2 v/v, effecting dissolution of the 6-APA. The approximate distribution of activity was:

|         | 1    | 2    | 3    | 4    |
|---------|------|------|------|------|
| AFA %   | 44.3 | 43.3 | 4.2  | —    |
| 6-APA % | 1.5  | 0.7  | 23.1 | 53.9 |

AFA could be recovered from the mixture eluted corresponding to the first and second columns, or recycled to fermentation depending on its proven concentration and characteristics. Likewise, but separately, 6-APA could be crystallized out and isolated using the mixture of eluates corresponding to the third and fourth columns by adjusting the pH to the isolelectric point for that product.

EXAMPLE 2

The biomass was separated out from a fermentation broth by filtration and the filtered broth was subjected to ultrafiltration in such a way that it was concentrated of the order of 30-fold, continuously, using a 20,000 Dalton membrane. The retained fraction was diafiltered to reduce the loss of penicillin activity. A second UF pass using a 2000 Dalton membrane was performed on the permeate plus diafiltrate, likewise as a continuous process.

This yielded a permeate with approximately 20 g/l of penicillin which had been sufficiently purified to allow enzyme conversion to be carried out in a recycling circuit in such a way that the penicillin was converted into 6-APA and phenylacetic acid with control of the reaction by keeping the pH constant in operations which required some 60–90 minutes.

The corresponding solution at the end of the enzyme conversion, consisting of a mixture in the aqueous phase of phenylacetic acid (AFA) in a concentration of the order of 7 g/l plus the 6-APA in a concentration of the order of 10 g/l, together with the other accompanying products resulting from fermentation, was passed through a suite of resins comprising a first column containing a resin of the non-ionic type, for example XAD 16, plus a further two columns packed with weak anionic resin of the IRA 68 type, regenerated and conditioned in the acetate form, followed by a further two columns with strong anionic resin of the SA 11A type similarly regenerated and conditioned as acetate.

The feed to column XAD 16 was such that a total of approximately 13 v/v of the final conversion solution was passed through in a descending flow at a rate of the order of 4 v/v.h and in such a way that the output from this resin provided the feed to the top of the first weak anionic resin column. Similarly the output from the bottom of this first anionic column provided the feed to the top of the second anionic resin column and so on until it had passed through the set of all four columns. When delivery to the non-ionic column was complete, it was flushed with 1 v/v of water, which was added to the volume fed to the first anionic resin column.

At this point it could be considered that the XAD 16 resin had performed its task by checking that it did not absorb AFA or 6-APA, and could be regenerated, even though the corresponding wastes produced were of no use. It was found that a residue containing of the order of 4–10 g/l of solids requiring disposal was eluted.

6 v/v of 0.05N NaCl solution was passed through the first weak anionic column in such a way that the quantity of 6-APA retained was displaced and fed to the second column. This in turn was flushed with 2.5 v/v of the same solution using a similar procedure. In this way the first and second columns became selectively charged with AFA while the third and fourth columns were charged with 6-APA. Each column was then eluted separately, using a 1M NaCl solution in each case. The first and second columns were eluted with 3 v/v, collecting the AFA and the third and fourth columns were eluted with 2 v/v to obtain a solution of 6-APA. The approximate distribution of activity was:

|         | 1    | 2    | 3    | 4    |
|---------|------|------|------|------|
| AFA %   | 13.1 | 68.2 | 4.4  | —    |
| 6-APA % | —    | 23.5 | 34.0 | 18.7 |

AFA could be recovered from the mixture eluted corresponding to the first and second columns, or recycled to fermentation depending on its proven concentration and characteristics. Likewise, but separately, 6-APA could be crystallized out and isolated using the mixture of eluates corresponding to the third and fourth columns by adjusting the pH to the isolelectric point for that product.

What is claimed is:

1. A process for obtaining a 6-amino penicillanic and phenylacetic acid product from a culture broth in which a penicillin-producing microorganism has undergone fermentation to form penicillin having a ring structure containing a side chain linked to an amine group in position 6 of the ring thereof, said culture broth comprising the biomass of the microorganism and products of the fermentation, including the penicillin, consisting essentially of the following successive steps:

(a) purifying the penicillin containing culture broth by (i) separating the biomass or a portion thereof from the culture broth and then (ii) ultrafiltrating the remaining culture broth with at least one filter having a molecular cut-off size in a range of from 20,000 to 2,000 Dalton to separate the penicillin and other products of the fermentation that pass through the at least one filter from the remainder of the products of the fermentation and from any remaining biomass, said ultrafiltration process forming an ultrafiltrate containing the penicillin and the other products that pass through the at least one filter, (b) treating the ultrafiltrate with an enzyme that catalyzes the removal of the side chain linked to the amine group in position 6 of the ring of the penicillin to form an enzymatically converted ultrafiltrate comprising 6-aminopenicillanic acid and phenylacetic acid;

(c) separating the 6-aminopenicillanic acid and phenylacetic acid by fractionated sequential separation using exchange resins; and (d) recovering the 6-aminopenicillanic acid, the phenylacetic acid or both.

2. A process according to claim 1, wherein the ultrafiltrating in step (a) is performed in successive steps with a plurality of filters each of which has a molecular cut-off size within the range of from 20,000 to 2,000 Dalton.

3. A process according to claim 2, wherein the treatment in step (b) is performed with a fixed enzyme.

4. A process according to claim 1, comprising recovering the 6-aminopenicillanic acid in step (d).

5. A process according to claim 4, comprising converting the 6-aminopenicillanic acid recovered in step (d) to a semisynthetic penicillin by chemical or enzymatic synthesis.

6. A process according to claim 5 wherein the semisynthetic penicillin is ampicillin or amoxycillin.

7. A process according to claim 1, comprising recovering the phenylacetic acid in step (d).

8. A process according to claim 7, comprising adding the recovered phenylacetic acid to a fermentation medium for synthesis of Penicillin G.

9. A process according to claim 1, wherein said penicillin is Penicillin G.

10. A process according to claim 1, wherein said penicillin is Penicillin V.

11. A process according to claim 1, wherein said biomass or portion thereof is separated from the culture broth in step (a) (i) by filtration.

12. A process according to claim 1, wherein the 6-aminopenicillanic acid is recovered in step (d) by crystallization.

* * * * *